US00PP37683P2

(12) United States Plant Patent
Hansen

(10) Patent No.: US PP37,683 P2
(45) Date of Patent: Sep. 8, 2026

(54) ***DICENTRA* PLANT NAMED 'Hearts on Fire'**

(50) Latin Name: *Dicentra spectabilis*
Varietal Denomination: Hearts on Fire

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 19/729,050

(22) Filed: Feb. 25, 2026

(51) Int. Cl.
*A01H 5/02* (2018.01)
*A01H 6/64* (2018.01)

(52) U.S. Cl.
USPC ..... Plt./426

(58) Field of Classification Search
USPC ..... Plt./426
See application file for complete search history.

*Primary Examiner* — Susan Mccormick Ewoldt

(57) ABSTRACT

A new and unique Old-fashioned Bleeding Heart, *Dicentra* plant named 'Hearts on Fire' characterized by large habit and deeply-lobed triternate foliage. The leaves emerge bright gold with reddish blush. The plant has large flowers that are heart-shaped deep reddish surrounding white center petals, on outwardly arching racemes, and stays in bloom 4 to 5 weeks beginning late spring. The new plant has an excellent growth rate.

2 Drawing Sheets

Botanical classification: *Dicentra spectabilis.*
Variety denomination: 'Hearts on Fire'.

STATEMENT REGARDING PRIOR DISCLOSURES UNDER 37 CFR 1.77(B)(6)

The Applicant asserts that no publications or advertisements relating to sales, offers for sale, or public distribution occurred more than one year prior to the effective filing date of this application. The first offer for sale was by Walters Gardens, Inc. on Apr. 4, 2025, to Mariani Nursery. Walters Gardens, Inc. obtained the new plant and all information about the new plant directly from the inventor. Any information or disclosure about the claimed plant less than one year prior to the effective filing date of this application would have been obtained directly or indirectly from the Inventor and would be a 35 U.S.C. 102(b) exception.

BACKGROUND OF THE INVENTION

The present invention relates to the new and distinct *Dicentra spectabilis* 'Hearts on Fire' hereinafter referred to by the cultivar name 'Hearts on Fire' and the new plant. 'Hearts on Fire' is the result of a self-pollination of the proprietary unnamed hybrid known only by the breeder code 12-8-1 (not patented) on Jun. 19, 2019, at a wholesale perennial nursery in Zeeland, Michigan, USA. Through trials at a wholesale perennial nursery the plant was referred to by the to by the code 19-2-4. The new plant has been successfully asexually propagated initially by stem cuttings in 2021 followed by shoot tip tissue culture at the same nursery in Zeeland, Michigan. Both these asexual propagation systems have been found to produce stable and identical plants that maintain all the unique characteristics of the original plant in successive generations.

BRIEF DESCRIPTION OF THE INVENTION

The new plant can be most closely compared with: 'Ruby Gold' (not patented), 'Gold Heart' (not patented), and 'Hordival' U.S. Plant Pat. No. 22,739.

'Ruby Gold' has more chartreuse foliage without the reddish blush on the new leaves, the flowers are slightly lighter reddish, the outer petal apices are more perpendicular to the center axis, the peduncles and pedicels less intense reddish coloration. 'Gold Heart' lighter pinkish flowers and less dense and more open habit, and the foliage does not have the burgundy tinting. 'Hordival' has a larger habit, the foliage is deep green colored, and the flowers are more orangish-red.

The parent plant has a taller more open habit and the flowers were not as dark reddish coloration.

The new plant, 'Hearts on Fire', is unique from all Old-fashioned Bleeding Hearts known to the inventor by the following combined traits:

1. Large habit with deeply lobed triternate foliage emerges bright gold with reddish blush;
2. Large flowers are heart-shaped deep reddish with white center petals beginning in late spring and continuing for four to five weeks;
3. Racemes arch outwardly.

BRIEF DESCRIPTION OF THE DRAWINGS

The color drawings illustrate the overall characteristics of the new plant and demonstrate the overall appearance of the new plant including the unique traits as a four-year-old plant growing in a full-sun trial garden in Zeeland, Michigan with supplemental water and fertilizer as needed. The colors are as true as reasonably possible given the technology available. The colors are as accurate as reasonably possible with color reproductions. Ambient light, spectrum, temperature, source, duration and direction may cause minor variation in appearance.

DETAILED DESCRIPTION OF THE INVENTION

Figure 1:
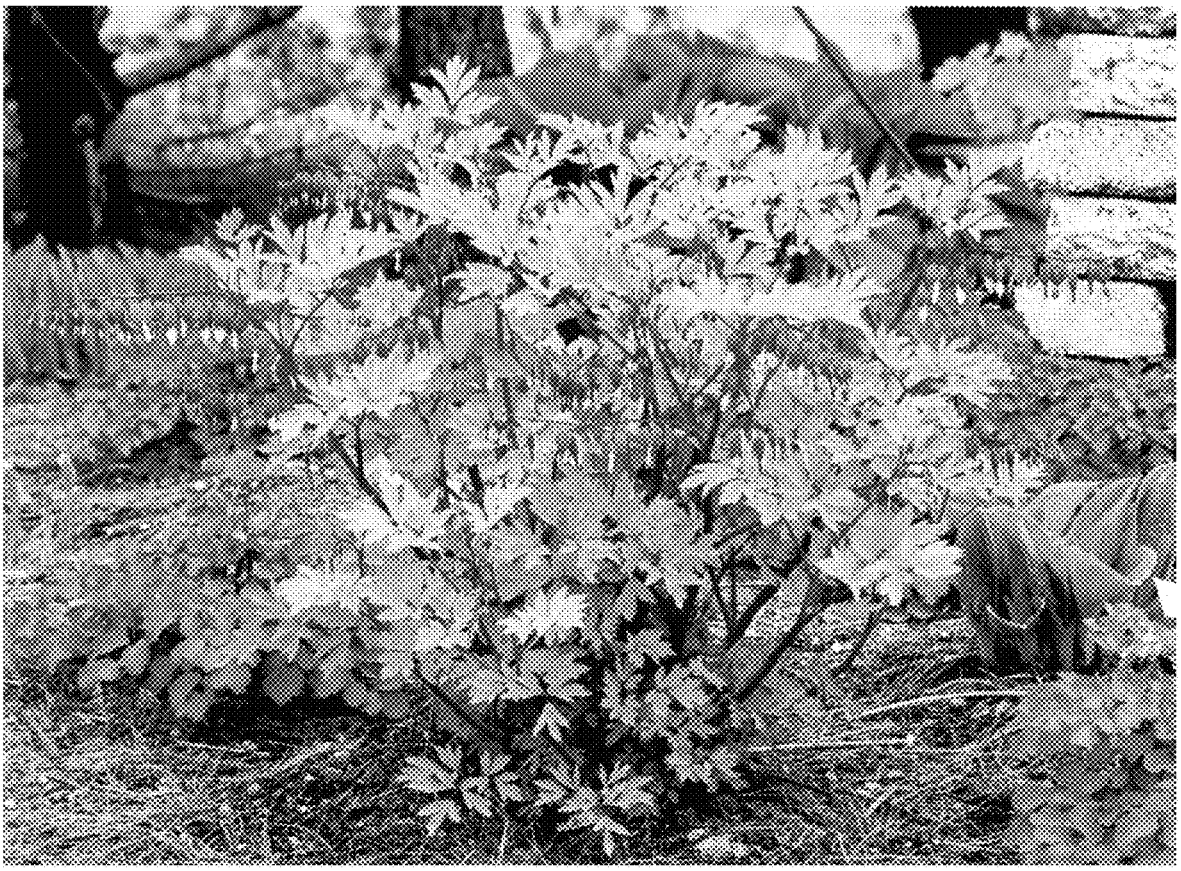
FIG. 1 shows the new plant grown in a partial-sun trial garden.
Figure 2:
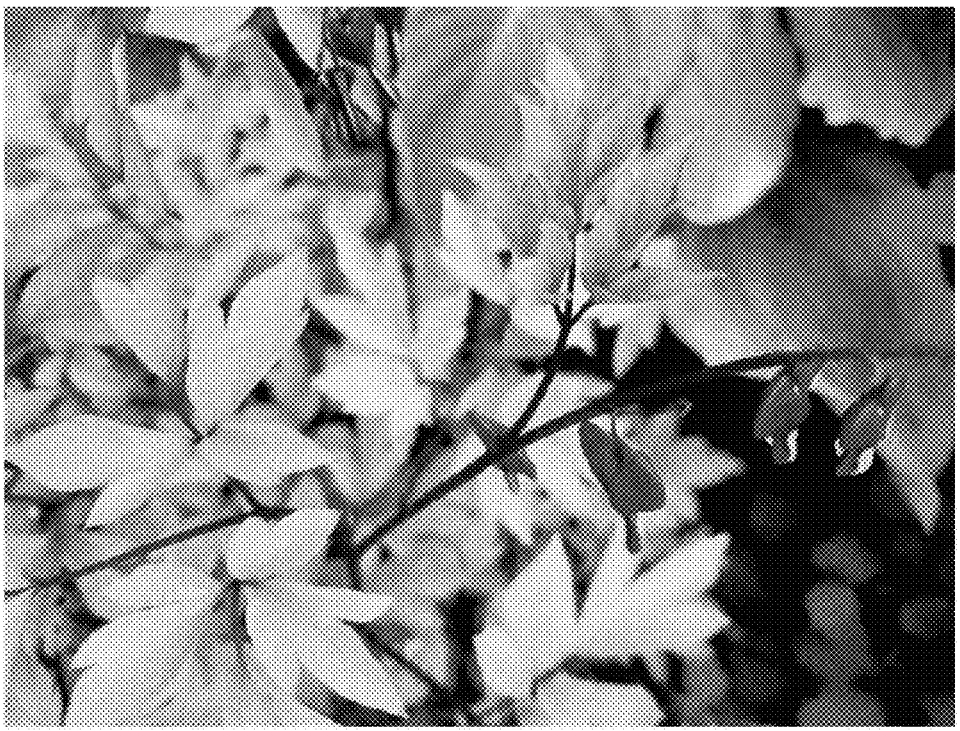
FIG. 2 shows close-up of the young foliage with reddish blush.
Figure 3:
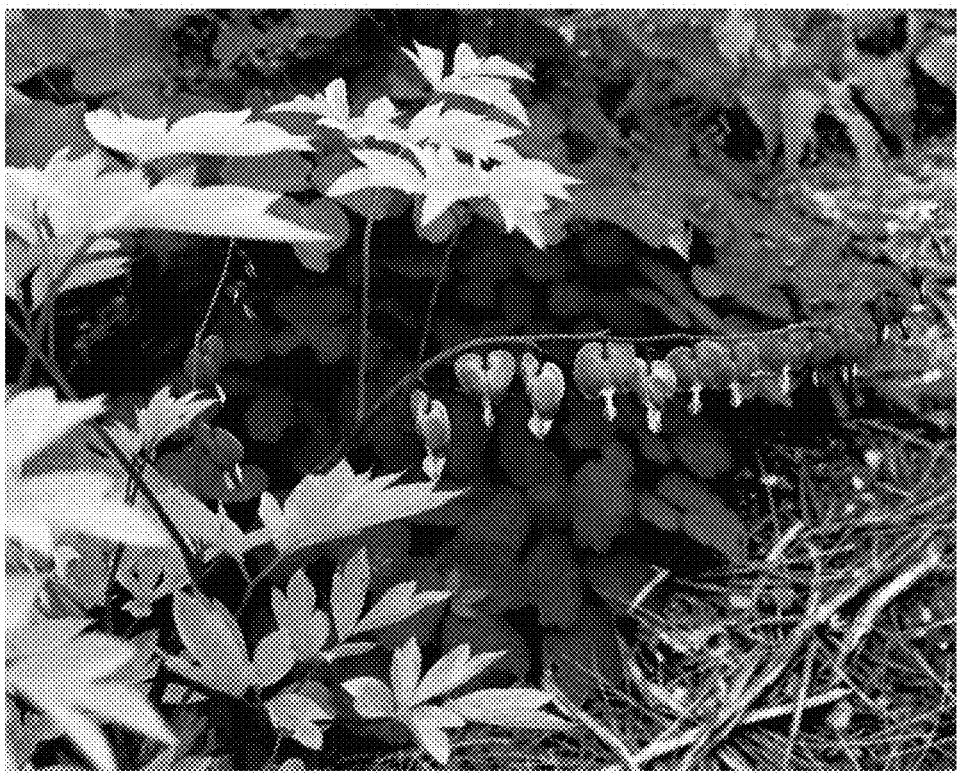
FIG. 3 shows a close-up of the flowers and buds in decreasing maturity from left to right.

The following detailed description is based on a four-year-old plant growing in a full-sun trial garden in Zeeland, MI, USA. Except for ordinary dictionary color usage, color references are according to The Royal Horticultural Society Colour Chart, 2015 edition.

Parentage: Female and male parent is 12-8-1;

Asexual propagation: Plant tissue culture, time to finish from a 65 mm plug to a 3.8-liter container about 5 weeks following vernalization;

Roots: Thick, fleshy, with finely branching tips; color nearest RHS 159D depending on soil substrate and nutrition;

Plant habit: Herbaceous, winter-hardy perennial; forming compact mound with about 10 stems;

Size: Foliage grows to 56 cm tall to top of foliage and 74 cm wide; flowering to 54 cm tall and 106 cm wide; foliage becomes dormant in the heat of summer;

Stem: Cylindrical; glabrous; to 63 cm long and 8 mm diameter at base;

Stem color: Proximally between RHS 160C and RHS 162C with strong blush of nearest RHS 183A; distally nearest RHS 187A;

Vigor: Excellent; growing best in well-drained soil in partly shade conditions;

Leaf: Triternate to irregularly divided; deeply lobed; deltoid in outline; to 17 cm long and 16 cm wide; glabrous adaxial and abaxial;

Primary leaflets: To about 8.4 cm long and 9.3 cm wide;

Secondary leaflets: 2 to 5-lobed; overall outline rhomboid; center leaflet to about 5.3 cm long and 6.2 cm wide; side leaflet to about 6.0 cm long and 4.4 cm wide;

Lobes: Oblanceolate to lanceolate; apex acute, base fused with other lobes in the proximal one-quarter; margin entire; to about 4.9 cm long and 1.4 cm wide;

Leaf color: Emerging and developing adaxial nearest RHS 2B, emerging and developing abaxial nearest blend of RHS 146D and RHS N148C, with a thin margin and light blush of nearest RHS 187B more concentrated near the apex of both adaxial and abaxial; mature adaxial between RHS N144B and RHS 151B, mature abaxial between RHS 146D and RHS N148C;

Venation: Pinnate; glabrous adaxial and abaxial; costate abaxial; slightly indented abaxial;

Vein color: Adaxial between RHS N144B and RHS 151B, abaxial nearest RHS 146D;

Petiole: Cylindrical with adaxial proximal portion grooved channel; glabrous; flexible; to 10 cm long and 4 mm across above clasping base, base to about 3 mm across;

Petiole color: Between RHS 183A and RHS N186C;

Rachis: Cylindrical with adaxial grooved channel; glabrous; flexible; to 4.9 cm long and 2 mm diameter;

Petiolule: Cylindrical with adaxial grooved channel; glabrous; flexible; to 2 cm long and 2 mm diameter;

Rachis and petiolule color: Nearest RHS 183D;

Inflorescence: Raceme; about 13 per plant; aspect outwardly;

Number of flowers: About 10 to 28 per raceme;

Peduncle: Cylindrical; glabrous; slightly lustrous; to 22 cm long and 3 mm diameter; aspect outwardly;

Peduncle color: Proximally nearest RHS 187A, distally between RHS 183D and RHS 59B;

Pedicel: Cylindrical; glabrous; slightly glaucous; to about 10 mm long and about 0.7 mm diameter; subtended by foliar bract about 6 mm long and 1 mm wide at base;

Pedicel color: Between RHS 183D and RHS 59B;

Foliar bract: Linear; glabrous; narrowly acute margin; truncate base; entire margin; to about 6 mm long and 1 mm across at base; color between RHS 183D and RHS 59B;

Flower bud: One day prior to opening inverted vase-shaped, narrowest in middle; base cordate; apex acute; to about 30 mm long, 18 mm wide and 7 mm thick at the base, about 3.5 mm diameter in middle and near apex 5.0 mm across with wings extending to about 8 mm across;

Flower season: Beginning early May and continuing for about 4 to 5 weeks;

Flower lastingness: Individual flower last about one week; each raceme lasts about 3 weeks;

Bud color: One day prior to opening proximally nearest RHS 53B and at the narrow portion nearest RHS 53A, distal petal arms nearest RHS 53B, distal protruding wings hyaline to nearest RHS NN155D;

Flower: Zygomorphic; proximally cordate; laterally slightly applanate; with two sets of petals; about 33 mm long, 23 mm wide near base, 11 mm thick, 3 mm wide at constriction, 26 mm wide at reflexed outer petal apices, 3.5 mm wide near inner petal apex, protruding wings to 9 mm wide;

Corolla: Outer petals opposite, inflated proximally, concavo-convex and reflexed distally, glabrous, fleshy and stiff; apex acute, basal 3 mm fused to opposite petal; margin entire, to 33 mm long extended and 12 mm long in reflexed state, 11 mm wide near base, and 3.5 mm wide from constriction to near apex; outer petal color abaxial base between RHS 51A and RHS 53B, abaxial apex nearest RHS N155D; adaxial nearest RHS N155B, heavily maculate more concentrated distally with between RHS 51A and RHS 58A, with base and distal veins nearest RHS N155D; inner petals opposite, at right angle to outer set; spatulate with proximal portion fleshy and cupped, apex acute and fused in distal 1 mm; to about 26 mm long and 4 mm wide in constricted portion, 5 mm wide in basal 15 mm, with keeled, central, protruding wing in distal 12 mm extending about 3 mm; inner petal color adaxial proximal cupped portion nearest RHS N155B, moderately maculate with between RHS 51A and RHS 58A, central portion at base of wing nearest RHS 5C on margins and nearest RHS NN155D in the center, apical 5 mm nearest RHS N79A with the margin nearest RHS NN155D; inner petal color abaxial proximal cupped portion nearest RHS N155B, moderately maculate with between RHS 51A and RHS 58A, central portion at base of wing nearest RHS 5C on margins and nearest RHS NN155D in center, wing nearest RHS NN155D, apical 5 mm nearest RHS NN155D with undertone of nearest RHS N79A;

Sepals: Not observed;

Gynoecium: Single; 20 mm long; erect, straight;

Style: About 7 mm long and 1 mm diameter at ovary, tapering toward stigma; persists with mature fruit; color nearest RHS 157B;

Stigma: With two apices about 1.5 mm long protruding from a base about 1.5 mm across and 1 mm thick; color nearest RHS 162A;

Ovary: Oblong; fusiform, tapering toward style and base; apex acute; base truncate; 12 mm long and 2 mm diameter near middle; color nearest RHS 145C in the proximal two-thirds and nearest RHS 157D in the distal one-third;

Androecium: Six; anthers and distal one-half of filaments connate into two groups;

Filaments: Six; petaloid; arcuate 180 degrees in the basal 5 mm, fused in a 3 mm long section about 3 mm from anther, free in distal 3 mm; petaloid bases separate; in two groups at right angle to inner petals; two lateral and one central petaloid in each group; two lateral filaments to about 3 mm wide near base and about 27 mm long stretch, central filament to about 2 mm wide near base and about 27 mm long stretched, both lateral and central filament narrowed to about 0.2 mm diameter in distal 6 mm; color between RHS 75D and RHS 65D with apical narrowed portion nearest RHS NN155D;

Anthers: Closely arranged just below stigma; ellipsoidal; longitudinal; about 2.7 mm long and 1 mm across; color nearest RHS 10A;

Pollen: Abundant; color nearest RHS 13C;

Fragrance: Not detected;

Fruit: 2-valved dehiscent capsule; lanceolate; glabrous; apex tapering to style; base attenuate; slightly arcuate and varicose with individual seeds; to about 20 mm long and 3 mm across;

Fruit color: When mature nearest RHS 145A with top portion exposed to high sun nearest RHS 183B to strongly maculate with nearest RHS 183B;

Seed: About seven per fruit; ellipsoidal; arillate; lustrous; to about 2 mm long and 1.5 mm across; color variable, vitreous, white nearest RHS NN155D, to nearest RHS 177B;

Pest and disease tolerance: 'Hearts on Fire' has not shown susceptibility to insects of the sub-families Aphidoidea and Aleyrodoidea or fungi of unknown scientific names that are frequent pests and diseases of other cultivars in the genus *Lamprocapnos*.

I claim:

1. A new and distinct cultivar of Old-fashioned Bleeding Heart, *Dicentra* plant named 'Hearts on Fire' as herein described and illustrated.

* * * * *